United States Patent [19]

Alarcon

[11] Patent Number: 5,718,666
[45] Date of Patent: Feb. 17, 1998

[54] TRANSILLUMINATING BOUGIE

[75] Inventor: Sean D. Alarcon, Santa Barbara, Calif.

[73] Assignee: Bioenterics Corporation, Carpinteria, Calif.

[21] Appl. No.: 609,914

[22] Filed: Feb. 29, 1996

[51] Int. Cl.$^6$ ......................................................... A61B 1/07
[52] U.S. Cl. .............................. 600/249; 362/32; 385/901
[58] Field of Search ..................................... 606/2, 13, 15, 606/17; 607/88, 93; 600/204, 184, 199, 201, 245, 128, 129, 170, 171, 182, 249; 362/804, 32; 385/125, 147, 901, 902

[56] References Cited

U.S. PATENT DOCUMENTS

| | | | |
|---|---|---|---|
| 1,677,016 | 7/1928 | Berry | 607/93 |
| 1,794,557 | 3/1931 | Symonds | 607/93 |
| 4,195,907 | 4/1980 | Zamja et al. | 385/125 |
| 4,249,795 | 2/1981 | Jones | 385/902 X |
| 4,782,818 | 11/1988 | Mori | 607/93 X |
| 5,006,106 | 4/1991 | Angelchik. | |
| 5,432,876 | 7/1995 | Appeldorn et al. | 362/32 X |
| 5,617,497 | 4/1997 | Kingstone | 385/901 X |

*Primary Examiner*—Jeffrey A. Smith
*Attorney, Agent, or Firm*—Michael G. Petit

[57] ABSTRACT

A light-conducting bougie consisting of an elongate flexible member operable for conducting light from the proximal end of the bougie to the distal portion thereof. The light-conducting bougie is made from a substantially homogenous, optically transparent polymer being flexible and operable for the transmission of light. The bougie is particularly useful for transilluminating tissue within a body. In operation, the distal end of the bougie is inserted into a hollow tissue such as the esophagus by passage through the mouth. Illuminating light from a light source enters the proximal end of the bougie and is conducted to the distal portion thereof to exit the bougie and transilluminate the surrounding wall of the organ or structure. The present invention provides an improved bougie wherein the intensity of the portion of light directed radially outward from the distal end portion of the bougie is increased without the addition of material scattering centers to the polymeric body. The improved lateral deflection of transillumination light from the bougie is due to the intentional formation of one or more voids disposed within the homogenous polymer forming the distal end portion of the bougie. The void and the polymer have different indices of refraction which cause lateral reflection and/or refraction of light propagating axially through the bougie at the polymer/void interface.

14 Claims, 3 Drawing Sheets

TRANSILLUMINATING BOUGIE

BACKGROUND OF THE INVENTION

1. Field of the Invention

This invention relates to a surgical illumination instrument and more particularly to a flexible light-conducting bougie for insertion into a portion of the body to conduct light from external light source into the portion of the body, the light thereafter to transilluminate tissue surrounding the distal portion of the bougie.

2. Prior Art

A light-conducting bougie is an elongate flexible light pipe useful for conducting light from an external source of light to the interior of a hollow tissue within a person's body. The distal end of a flexible bougie includes the transilluminating portion and is adapted to be introduced into a body cavity such as the esophagus, stomach or rectum by insertion and advancement through the mouth or anus. In skilled hands, the distal end of an orally inserted bougie may even be advanced beyond the stomach into the duodenum. Following placement of the distal end of a light-conducting bougie within the hollow structure of interest, light is introduced by light coupling means into the proximal end of the bougie and conducted by means of the body portion of the bougie to the distal end portion thereof wherein a portion of the light is deflected or scattered from within the bougie to illuminate the surrounding tissue. A portion of the light which illuminates the surrounding tissue will pass through the tissue and is referred to herein as "transilluminating" light.

Such transillumination of tissue is particularly useful in endoscopic surgery in general and laparoscopic surgery in particular. During laparoscopic surgery, a surgeon works through one end of a cannula or hollow tube wherein the opposite end of the cannula or hollow tube is positioned within the peritoneal cavity of a patient. All surgical instruments are manipulated through one or more such cannula while the operative field is viewed through a camera disposed within the peritoneal cavity through a dedicated viewing cannula. With certain procedures such as laparoscopic fundoplication, it is particularly desirable to have a clear view of the gastro-esophageal junction. Such a view may be attained by transilluminating the esophagus by means of a light-conducting bougie having a distal end comprising a diffuser element. The distal end of the bougie is introduced into the esophagus by means of the nose or mouth and advanced until the distal end is adjacent to the gastro-esophageal junction. Such a bougie and a method for using the bougie is disclosed, for example, in U.S. Pat. No. 5,006,106 to Angelchik.

The advantages of using a light-conducting bougie positioned within the esophagus to transilluminate the surrounding esophageal tissue during laparoscopic surgery include improved visibility of the structures within the operative field and the reduction in the number of cannulas for conducting light from external light sources within the operative field. It is, however, a disadvantage of standard light-conducting bougies in that much, or even most of the light exits the bougie axially through the distal tip. Thus, there is relatively little light exiting radially (i.e. perpendicular to the long, central axis of the bougie) in any particular portion of the bougie. It is common in the art to embed material scattering centers within the (otherwise optically transparent) elastomer material comprising the bougie which scattering centers serve to scatter light radially from the bougie to illuminate the surrounding tissue with a more or less cylindrical distribution of light. While such heterogeneous compositions improve the lateral scattering of light from the bougie along the heterogeneous, the construction requires adding impurities to an otherwise homogenous transparent elastomer which impurities may: (a) not be biocompatible with the human body and/or (b) tend to compromise the structural integrity of the body portion of the bougie. Compromising the structural integrity of the bougie by introducing heterogeneity into the polymeric bougie body may result in breakage, with a non-biocompatible scattering center (foreign body) inadvertently being left within the patient.

Brown et al in U.S. Pat. No. 5,292,320 disclose a light delivery catheter employing a fiber optic to induce hyperthermia in a target tissue by delivering laser light to the target tissue adjacent to, but spaced from, the distal end thereof. To prevent heating of intervening non-target tissue by the catheter, Brown et al provide a series of reflective surfaces along the fiber to direct the laser light toward the target tissue and focus the light thereon. Each reflective surface comprises a notch cut transversely in the edge of the fiber optic core. One non-reflecting edge of the generally "v" shaped notch is perpendicular to the central axis of the fiber, while the other reflecting edge is tilted at an angle calculated to reflect axially directed light to the target tissue. The reflective surface of each notch, being distal to the preceding notch, has a different tilt angle in order to reflect light to the target tissue. Thus, Brown et al avoid some problems encountered with catheters employing light diffuser tips for delivering light to tissue. The construction of Brown et al, while avoiding certain problems associated with incorporating particulate foreign bodies in an elastomer, is useful for delivering light only to a discrete target. The construction is not efficient or even operable for delivering diffuse transilluminating light to surrounding tissue.

It is, therefore, desirable to provide a transilluminating bougie having radial light diffusion operating characteristics comparable to light-conducting bougies presently used in the art but which does not require incorporation of non-biocompatible particulates or other foreign materials or scattering centers within the light-conducting material for operability.

SUMMARY OF THE INVENTION

It is an object of this invention to provide a bougie operable for transilluminating tissues within the body.

It is a second object of this invention to provide a light-conducting bougie operable for the efficient radial (non-axial) delivery of light from within the bougie wherein no material particulates are incorporated into the homogenous transparent light-conducting elastomer comprising the bougie.

The features of the invention believed to be novel are set forth with particularity in the appended claims however the invention itself, both as to organization and method of operation, together with further objects and advantages thereof may best be understood by reference to the following description taken in conjunction with the following drawings in which:

DESCRIPTION OF THE PREFERRED EMBODIMENTS

Figure 1:
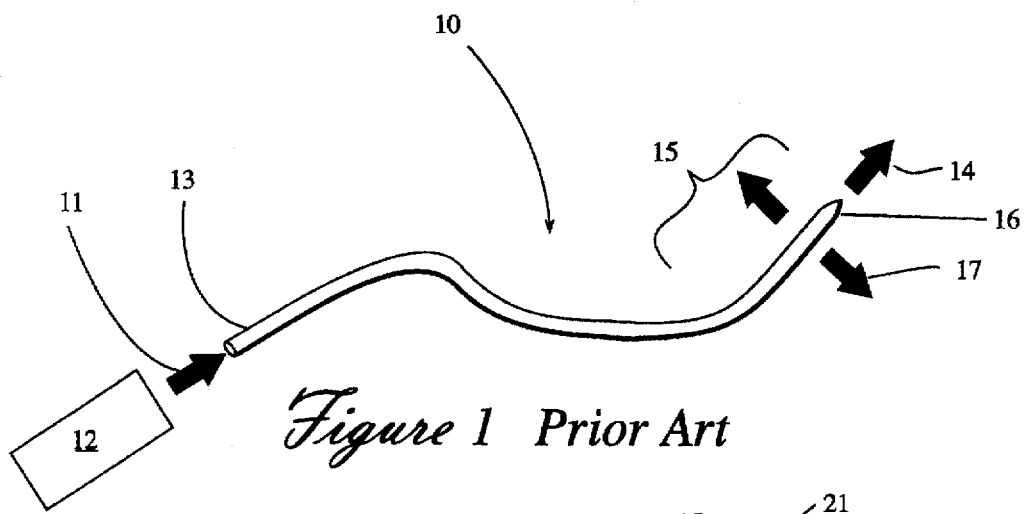
FIG. 1 is a perspective view of a light conducting bougie in accordance with the prior art.

With reference to FIG. 1, a prior art bougie 10 conducts light 11 from the proximal end 13 from a light source 12 to the distal tip 16 of the bougie 10. A portion 17 of the light 11 exits the distal end portion 15 laterally in a radial direction. The terms "radial" and "radially", or in the alternative, "lateral" or "laterally" refer to a direction extending away from the central axis of a bougie and not parallel thereto. A second portion 14 of light 11 exits axially through the distal tip 11. In certain tissue transillumination applications it is desirable to maximize the lateral portion 17 of light 11 and minimize the axial portion 14 of light 11 which axial portion 14 may cause unwanted heating at the distal tip 11.

In the prior art, it is well known to employ material interfaces having dissimilar indices of refraction to cause either reflection or refraction of light conducted through a first material when the light impinges on the interface between the first material and a second material having a different index of refraction. Such material interfaces provide, for example, means for redirecting light transmitted along the length of a bougie in an axial direction into a tissue positioned laterally to the long axis of the bougie, as for example, by forming the first material into a conical indentation at the distal tip 16 thereof and filling the conical indentation with a second material having a different index of refraction than the first material. Alternatively, the distal tip 16 of an elongate bougie 10 can be beveled (not shown) to reflect axially conducted light 11 laterally at a desired angle. In order to improve radial scattering of light 11 from the distal end portion 15 of the bougie 10 adjacent to the distal tip 11, it is well known in the art to include scattering centers (not shown) within the distal end portion 15 of the bougie 10. Commonly used scattering centers include metal particulates or compositions such as barium sulfate or silica. While such devices may be particularly useful for certain kinds of bougies employing a high durometer light-conducting elastomer having a high degree of structural integrity or cohesiveness, such a construction may not be suitable for a softer, more flexible and less cohesive elastomer material which may be more easily broken and remain in the patient's body after the bougie is removed.

As mentioned earlier, a prior art light-conducting bougie of the type shown in FIG. 1 and its use is disclosed in U.S. Pat. No. 5,006,106 (hereinafter referred to as "'106") to Angelchik. The present invention provides an improvement in the bougie disclosed in '106 and involves modifying the distal end portion 15 of the bougie 10 which distal end portion 15 provides efficient lateral light delivery within the body.

Figure 2:
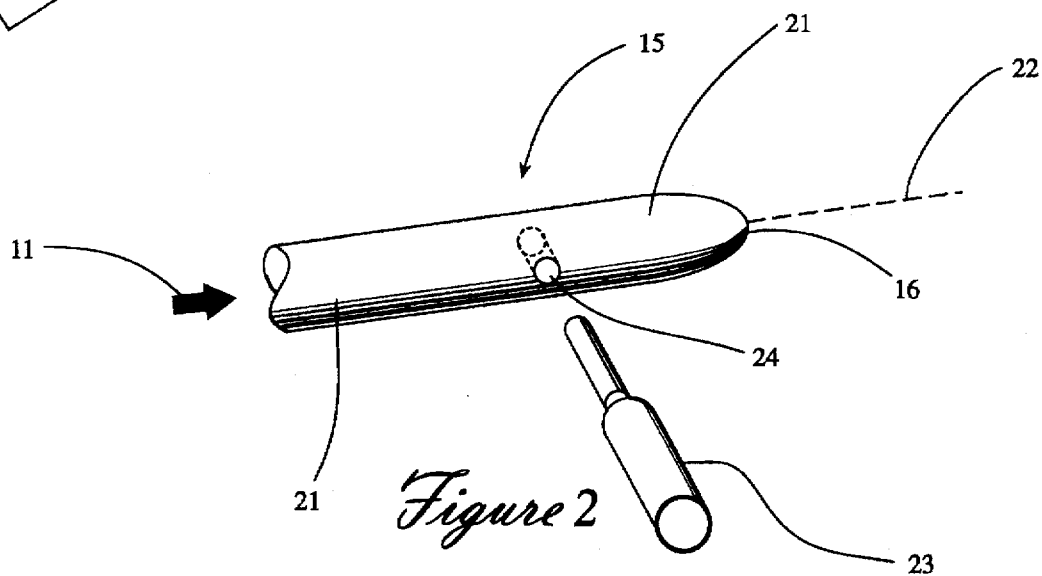
FIG. 2 is a fragmentary perspective view of the distal end portion of the prior art bougie shown in FIG. 1 with a cylindrical void therein disposed to intersect the central axis of the bougie at a finite angle thereto.

Turning now to FIG. 2, a bougie end portion 15 having a distal tip 16 is shown wherein a light beam 11 from a light source (not shown) is transmitting axially therethrough from left to right traveling toward the distal tip 16 of the bougie end portion 15. A cylindrical core (not shown) of elastomeric light-conducting material 21 is removed from the bougie distal end portion 15 by means of a coring tool 23 to provide a transverse cylindrical void 24 within the end portion having a void length (a cylinder height) approximately equal to the outer diameter of the cylindrical distal end portion 15 of the bougie 10. When the light beam 11 encounters the cylindrical void 24, a portion of the light beam 11 is caused to reflect laterally, away from the long axis of the bougie, particularly at right angles to the central axis (not shown) of the void 24. Thus, the creation of a cylindrical void within the transparent elastomeric light-conducting material 21 comprising the bougie 10 enhances the portion of light 11 which exits the bougie 10 in a radial direction orthogonal to the long axis 22 of the bougie distal end portion 15.

Figure 3:
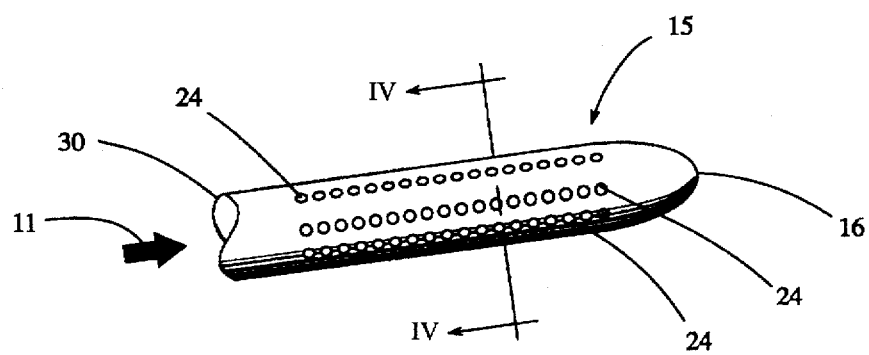
FIG. 3 shows a fragmentary perspective view of a second embodiment of the distal end of a bougie tip in accordance with the present invention wherein the distal end portion of the bougie includes a plurality of identical cylindrical voids disposed along the length of the distal portion.
Figure 4:
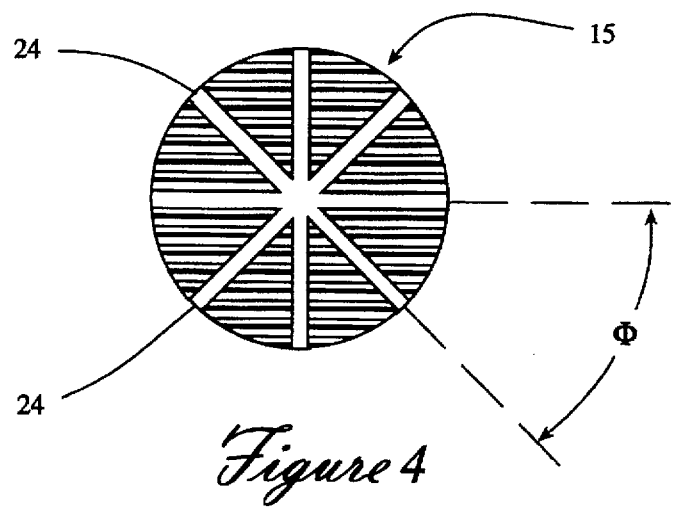
FIG. 4 shows a cross-sectional view of the bougie distal end portion of FIG. 3 taken along section lines IV—IV.

A second embodiment of a distal end portion of a bougie in accordance with the present invention is shown in FIG. 3. The bougie end portion 15 has a distal tip 16 which, as with the previously described embodiment, is preferably rounded to facilitate insertion into a tissue such as an esophagus. The light-conducting material 21 forming the bougie end portion 15 is preferably a flexible, bio-compatible optically transparent elastomer such as silicone rubber. Light 11 from a light source (not shown) is conducted to the proximal end 30 of the bougie end portion 15, a portion of the light 11 thereafter to be conducted to the distal tip 16. On route, the light 11, generally shown at the broad arrow, encounters a series of transverse cylindrical voids 24 formed into hollow cylinders disposed within the distal end portion 15 with the cylinder axes radiating spoke-like radially outward from the long axis of the bougie end portion 15 at right angles thereto and are inclined with respect to adjacent voids at an angle θ. The cylindrical elastomer wall (not shown) surrounding the voids 24 at the elastomer-void interface presents a discontinuity in the index of refraction of the elastomer material 21. When light 11 encounters the index of refraction discontinuities at the material/void interface, a portion of the light 11 is reflected laterally outward prior to reaching the distal tip 11, the laterally reflected portion transilluminating surrounding tissue. The plurality of cylindrical voids arrayed as shown in FIG. 3 provides a more or less cylindrical distribution pattern of transilluminating light around the distal end portion 15 of the bougie. FIG. 4 is a section of the distal portion 15 of FIG. 3 taken along section line IV—IV showing three axially intersecting cylindrical voids 24.

Figure 5:
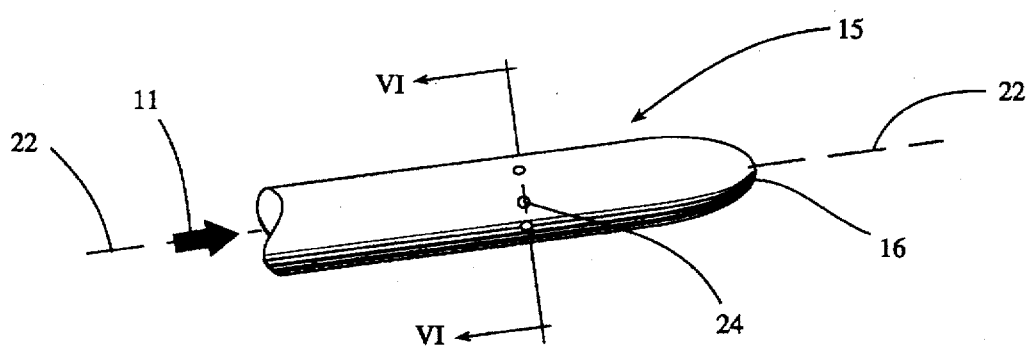
FIG. 5 is a fragmentary perspective view of a third embodiment of a bougie distal end portion illustrating three cylindrical voids disposed in the distal end portion wherein each void has a central axis which lies in the same plane as corresponding axes in the other voids and are perpendicular to the central axis of the bougie.

A simpler embodiment of the bougie distal end portion 15 of a bougie shown in FIG. 3 is shown in FIG. 5. In FIG. 5, a light beam 11 is conducted along the long central axis 22 of the distal end portion 15 of the bougie toward the distal tip 16 until the light 11 wavefront encounters the elastomer-void interface. In this embodiment, the cylindrical voids 24 are disposed within the distal end portion 15 of the bougie with the long axis 25 of each void 24 perpendicular to the long central axis 22 of the bougie end portion 15 and wherein the central axis of all cylindrical voids 24 lie in the same single plane as the other voids in a "cartwheel" configuration. Upon encountering the surface of the cylindrical void 24, a portion of the light beam 11 is reflected from the cylindrical surface of the void 24 to exit the distal end portion 15 of the bougie in a lateral direction. Although in the illustrated embodiment of FIG. 5 the voids 24 lie in the same place, the cylindrical voids 24 may be axially displaced from one another, the exterior opening of the voids 24 forming a spiral pattern upon the exterior surface of the distal end portion 15 of the bougie and each void inclined by an angle φ) with respect to adjacent voids.

Figure 6:
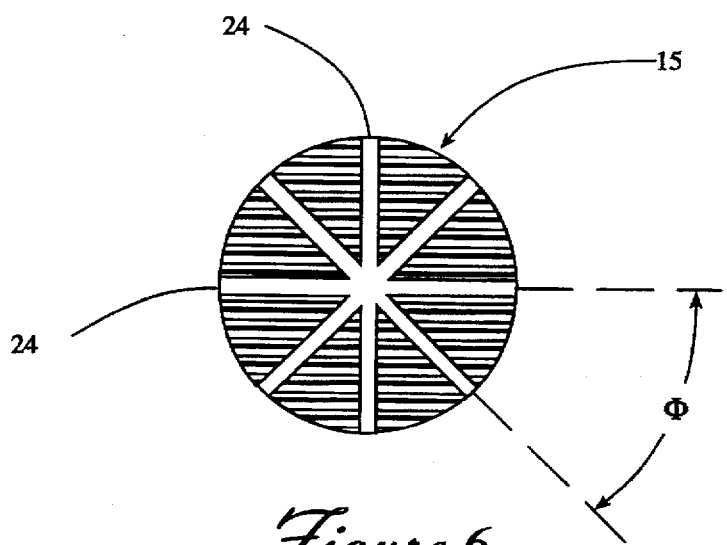
FIG. 6 shows a cross-section of the bougie tip of FIG. 5 taken along section line VI—VI.

FIG. 6 shows the cylindrical voids 24 within the bougie end portion 15 viewed along the section VI—VI of FIG. 5. Adjacent cylindrical voids 24 have central axes which intersect at the centers thereof at an angle φ with respect to each other. Such angular placement of the voids 24 preferably causes light 11 to reflect radially in three particularly preferred directions (which directions are in a plane orthogonal to the central longitudinal axis of the bougie and displaced by an angle φ from one another) rather than 360 degrees around the axis of the bougie which may be approximated by employing a large number of cylindrical voids 24 angularly displaced with respect to one another and disposed along the long axis of the distal end portion 15 of the bougie and perpendicular to the long axis thereof as shown in FIG. 3.

Figure 7:
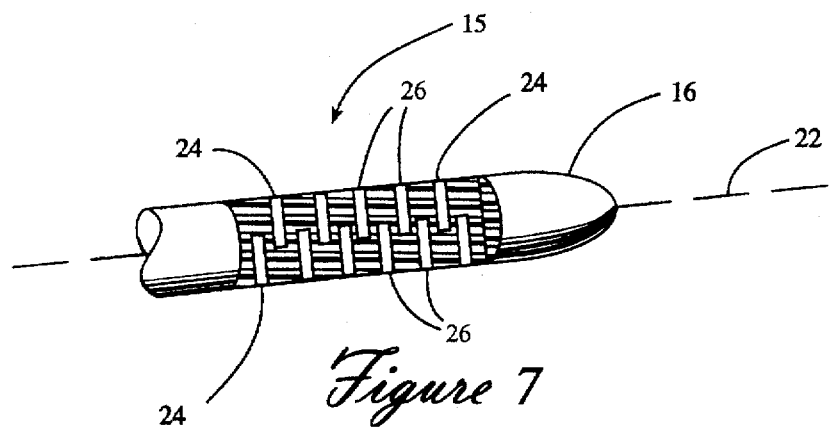
FIG. 7 is a fragmentary horizontal, partially sectional view of the distal end portion of a bougie wherein one end of the cylindrical void is occluded and fluid impermeable.

A further embodiment of the improved distal end portion 15 of the bougie 10 (FIG. 1) is shown in FIG. 7 wherein the cylindrical voids 24 are longitudinally displaced from one another along the long central axis of the bougie. In this embodiment one end of the voids 24 is sealed to form an air-pocket to inhibit fluid from entering the void 24 thereby changing the index of refraction of the void and the light reflectivity at the void-elastomer interface. One end of the voids 24 may be sealed as follows, provided that the opening thereinto is small, on the order of 0.5 mm or less. After the cylindrical voids 24 are formed in the light-conducting elastomer material 21 by suitable means such as coring or molding, the distal end portion of the bougie may be rapidly dip coated with a viscous clear light-conducting elastomer dispersion and the coat permitted to cure thereby sealing the ends of the cylindrical voids 24 with seals 26 against unwanted fluid entry.

Figure 8:
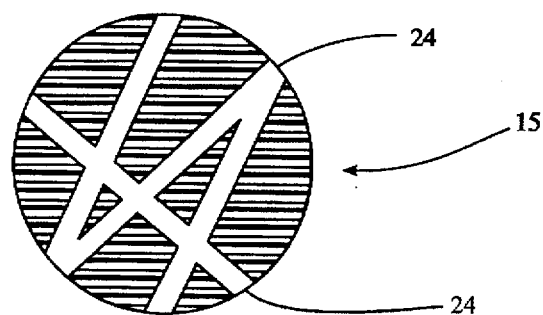
FIG. 8 shows a vertical cross-sectional view of the distal and portion of an embodiment of a distal end portion of a bougie similar to the end portion shown in FIG. 5 wherein two of the four cylindrical voids have a central axis which does not intersect the long central axis of the bougie.

Of course, not all cylindrical voids 24 need intersect the long central axis of the bougie. FIG. 8 is a cross-sectional view of the distal end portion (not shown) of a bougie similar to sections of the bougie distal end portions shown in FIGS. 4 and 6, but wherein not all of the cylindrical voids 24 pass through the central axis of the bougie.

Figure 9:
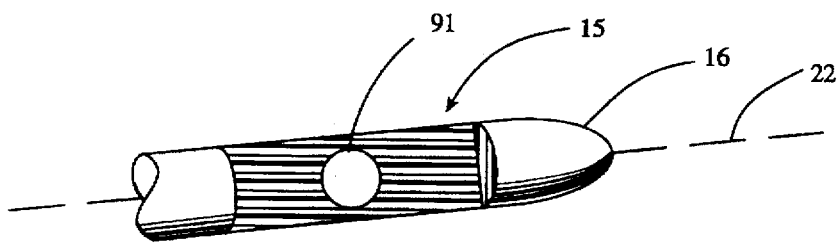
FIG. 9 is a partially cross-sectional elevational view of an embodiment of the distal end portion of a bougie containing a spherical void.

FIG. 9 is a partially cross-sectional perspective view of the distal end portion 15 of a bougie 10 (FIG. 1) wherein a spherical void 91 is symmetrically disposed within the distal end portion 15 so that an axis of rotational symmetry consisting of a straight line passing through the center of the spherical void lies upon the elongate central axis 22 of the distal end portion 15 of the bougie 10 (FIG. 1 ). The spherical void 91 has a void diameter of between 0.25 and 0.5 times the cylindrical body portion of the bougie diameter and the spherical void 91 has a center and a rotational axis of symmetry colinear with the central axis 22. Light (not shown) conducted in a direction parallel to axis 22 will reflect laterally outward at the void-elastomer interface thereby providing a symmetric lateral distribution of light for transilluminating surrounding tissue.

Figure 10:
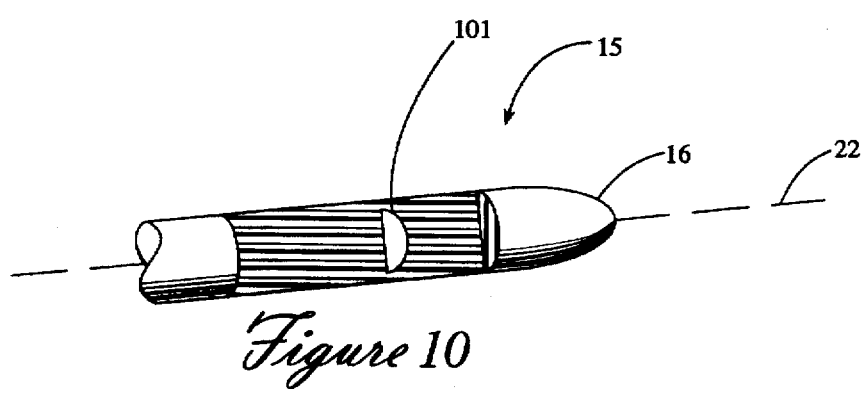
FIG. 10 is a partially cross-sectional elevational view of an embodiment of the distal end portion of a bougie wherein the void is semi-spherical.

In FIG. 10, the spherical void 91 of FIG. 9 is replaced with a semispherical void 101 having a circular cross-section wherein the rotational axis of symmetry of the void 101 coincides with the central axis 22 of the distal end portion 15. Such a semi-spherical void 101 may be piano-convex void wherein the convex surface of the void faces either toward or away from the distal tip 16. The semi-spherical void 101 has a void diameter of between 0.25 and 0.5 times the cylindrical body portion of the bougie diameter and the semi-spherical void 101 has a center and a rotational axis of symmetry colinear with the central axis 22. A void such as 91 or 101 may be formed within the bougie end portion by insertion molding the distal end portion 15 around a solvent extractable body having the desired void shape. After the bougie is formed, a small opening or conduit can be formed in the wall of the bougie end portion to provide solvent communication with the extractable body and dissolve the body leaving a complementary void in the elastomer. For the purpose of forming the extractable body, salt (NaCl) may be formed into a spherical bead or a planar convex lens by compression and conveniently embedded within the elastomeric bougie end portion. A solvent such as water can then be used to extract the body from the bougie distal end portion without effecting the elastomeric structure of the bougie distal end portion 15.

While particular embodiments of the present invention have been illustrated and described, it would be obvious to those skilled in the art that various other changes and modifications can be made without departing from the spirit and scope of the invention. For example, voids 24, 91 and 101 may be shaped and spaced along the bougie distal end portion 15 to adapt to a particular use or as preferred by a particular user. Elongate voids 24 open onto the outer surface of the distal end portion 15. The shape of the opening at the void-outer surface juncture may be triangular, square, rectangular, octagonal, circular, elliptical, semi-circular, star-shaped, oval or any combination thereof. It is therefore intended to cover in the appended claims all such changes and modifications within the scope of this invention.

What I claim is:

1. A device operable for receiving light from a light source and delivering the light to a cavity within an animal to diffusely illuminate the interior thereof, said device comprising an elongate flexible boogie having a proximal end adapted to receive light from a light source, a distal tip adapted for insertion within said cavity and an optically transparent cylindrical distal end portion therebetween, said distal end portion having a central axis, a cylindrical outer surface coaxial and coextensive with said central axis, said outer surface having a plurality of identical openings thereon, said plurality of openings projecting inwardly toward said central axis and traversing said distal end to form a plurality of elongate voids, said plurality of voids extending from opposite sides of said outer surface and traversing said distal end.

2. The device of claim 1 wherein each of said openings of said plurality of openings on said outer surface is circular.

3. The device of claim 1 wherein each of said openings of said plurality of openings on said outer surface is triangular.

4. The device of claim 1 wherein each of said openings of said plurality of openings on said outer surface is square.

5. The device of claim 1 wherein each of said openings of said plurality of openings on said outer surface is semi-circular.

6. The device of claim 1 wherein each of said openings of said plurality of openings on said outer surface is elliptical.

7. The device of claim 1 whereto each of said openings of said plurality of openings on said outer surface is octagonal.

8. The device of claim 1 wherein each of said openings of said plurality of openings on said outer surface is rectangular.

9. The device of claim 1 wherein each of said openings of said plurality of openings on said outer surface has the shape of a pentagram.

10. The device of claim 1 wherein each identical void of said plurality of elongate voids passes through the central axis of said distal end portion.

11. The device of claim 1 wherein at least one elongate void of said plurality of elongate voids passes through the central axis of said distal end portion.

12. A device for illuminating the interior of a body cavity comprising an elongate, flexible bougie having a proximal end adapted to receive light from a light source, a distal tip and an optically transparent cylindrical body portion therebetween, said cylindrical body portion having a central axis and an outer diameter, wherein said body portion further comprises a spherical void disposed therewithin, said spherical void having a void diameter between 0.25 and 0.5 times said outer diameter and wherein said spherical void has a center disposed on said central axis.

13. A device for delivering illuminating light to the interior of a body cavity comprising an elongate; flexible bougie having a proximal end adapted to receive light from a light source, a distal tip adapted for insertion into a body cavity and an optically transparent cylindrical body portion therebetween, said cylindrical body portion having a central axis and an outer diameter, wherein said body portion further comprises one semi-spherical void disposed therebetween, said semi-spherical void having a void diameter between 0.25 and 0.5 times said outer diameter of said cylindrical body portion and wherein said semi-spherical void has a rotational axis of symmetry disposed on said central axis.

14. A device operable for receiving light from a light source and delivering the light to a cavity within an animal to diffusely illuminate the interior thereof, said device comprising an elongate flexible bougie having a proximal end adapted to receive light from a light source, a distal tip adapted for insertion within said cavity and an optically transparent cylindrical distal end portion therebetween, said distal end portion having a central axis and a cylindrical outer surface coaxial and coextensive with said central axis, said outer surface having a plurality of identical and longitudinally displaced openings thereon and displaced from one another along the central axis of the distal end portion, said plurality of openings projecting inwardly toward said central axis and partially traversing said distal end to form a plurality of elongate voids, said plurality of voids extending from one side of said outer surface and partially traversing said distal end portion, and wherein ends of the plurality of elongate voids on the outer surface of the distal end portion are sealed off with clear, light conducting material to create air pockets in the elongate voids.

* * * * *